(12) United States Patent
Bittner

(10) Patent No.: US 10,136,894 B2
(45) Date of Patent: Nov. 27, 2018

(54) NERVE TREATMENT METHODS

(71) Applicant: BOARD OF REGENTS, THE UNIVERSITY OF TEXAS SYSTEM, Austin, TX (US)

(72) Inventor: George D. Bittner, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/597,891

(22) Filed: May 17, 2017

(65) Prior Publication Data

US 2017/0252041 A1 Sep. 7, 2017

Related U.S. Application Data

(63) Continuation of application No. 14/001,431, filed as application No. PCT/US2012/026764 on Feb. 27, 2012, now Pat. No. 9,955,973.

(60) Provisional application No. 61/446,803, filed on Feb. 25, 2011.

(51) Int. Cl.
| | | |
|---|---|---|
| A61B 17/08 | (2006.01) |
| A61B 17/11 | (2006.01) |
| A61M 5/00 | (2006.01) |
| A61B 17/00 | (2006.01) |
| A61B 90/00 | (2016.01) |

(52) U.S. Cl.
CPC .......... *A61B 17/1128* (2013.01); *A61M 5/00* (2013.01); *A61B 2017/00893* (2013.01); *A61B 2017/1132* (2013.01); *A61B 2090/0807* (2016.02)

(58) Field of Classification Search
CPC ........ A61B 17/1128; A61B 2017/1132; A61B 2017/00893; A61B 2090/0807; A61M 5/00
See application file for complete search history.

(56) References Cited

U.S. PATENT DOCUMENTS

| | | | |
|---|---|---|---|
| 4,306,561 A | 12/1981 | De Medinaceli | |
| 2003/0118545 A1* | 6/2003 | Shi ......................... | A61K 31/00 424/78.37 |
| 2004/0186489 A1 | 9/2004 | Lee | |
| 2007/0250082 A1 | 10/2007 | Kansoul | |
| 2010/0211172 A1 | 8/2010 | Bellamkonda et al. | |

FOREIGN PATENT DOCUMENTS

| | | |
|---|---|---|
| SU | 121532 | 8/1967 |
| SU | 1438738 | 11/1988 |

OTHER PUBLICATIONS

Polyethylene Glycol Rapidly Restore Axonal Integrity and Improves the Rate of Motor Behavior Recovery After Sciatic Nerve Crush Injury. Joshua M. Britt et al., May 5, 2010, J Neurophysiol 104: 695-703, 2010.*

(Continued)

*Primary Examiner* — Tuan V Nguyen
(74) *Attorney, Agent, or Firm* — Parker Highlander PLLC

(57) ABSTRACT

The present disclosure is directed to the use of fusogenic compounds such as polyethylene glycol (PEG) in combination with antioxidants, calcium-containing and calcium-free solutions for treating damaged nerves, such as for reconnecting severed nerves.

25 Claims, 12 Drawing Sheets

(56) References Cited

OTHER PUBLICATIONS

Bittner, G. D., et al. "Rapid, effective, and long-lasting behavioral recovery produced by microsutures, methylene blue, and polyethylene glycol after completely cutting rat sciatic nerves." *Journal of neuroscience research* 90.5 (2012): 967-980.
Britt, Joshua M., et al. "Polyethylene glycol rapidly restores axonal integrity and improves the rate of motor behavior recovery after sciatic nerve crush injury." *Journal of neurophysiology* 104.2 (2010): 695-703.
Krause, Todd. L., and George D. Bittner. "Rapid morphological fusion of severed my,relimted axons by polyethylene glycol.," *Proceedings of the National Academy of Sciences* 87.4 (1990): 1471-1475.
Lore, April B., et al. "Rapid induction of functional and morphological continuity between severed ends of mammalian or earthworm myelinated axons." *Journal of Neuroscience* 19.7 (1999): 2442-2454.
Stavisky, Ronda C., et al. "Melatonin enhances the in vitro and in vivo repair of severed rat sciatic axons." *Neuroscience letters* 376.2 (2005): 98-101.
International Preliminary Report on Patentability issued in International Application No. PCT/US2012/026764, dated Aug. 27, 2013.
International Search Report issued in International Application No. PCT/US2012/026764, dated Apr. 26, 2012.
International Written Opinion issued in International Application No. PCT/US2012/026764, dated Apr. 26, 2012.

\* cited by examiner

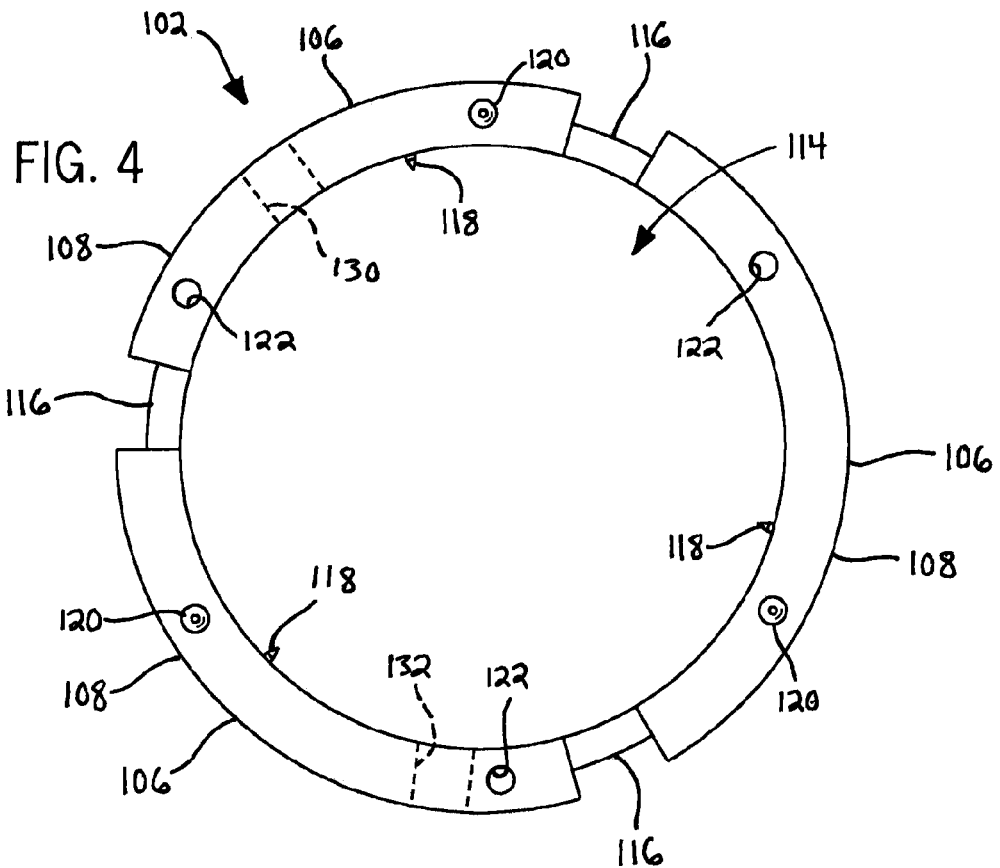
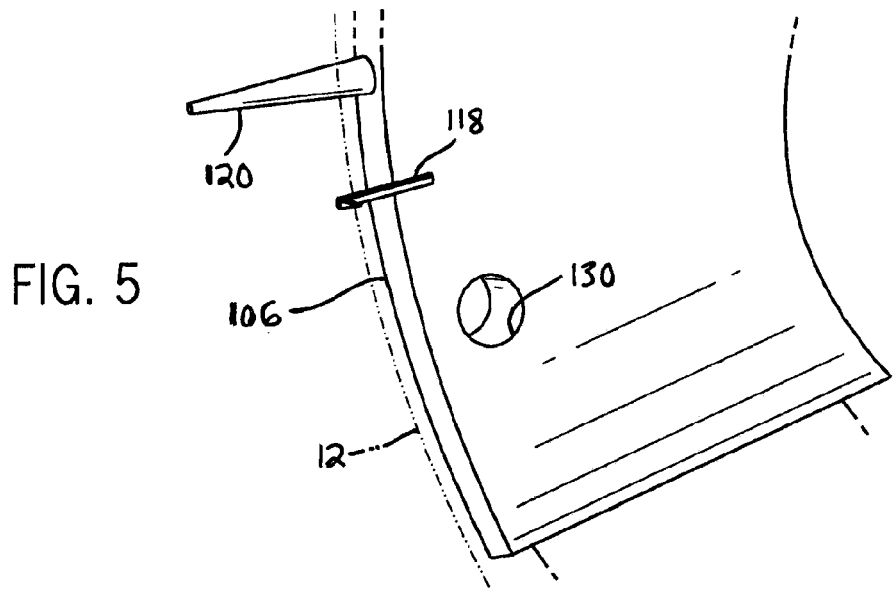

NERVE TREATMENT METHODS

CROSS-REFERENCE TO RELATED APPLICATION

This application is a continuation of U.S. application Ser. No. 14/001,431, filed Jan. 3, 2014, which is a national phase application under 35 U.S.C. § 371 of International Application No. PCT/US12/26764, filed Feb. 27, 2012, which claims the benefit of U.S. Provisional Patent Application No. 61/446,803, filed Feb. 25, 2011, the disclosures of which are hereby incorporated by reference in their entirety.

STATEMENT OF FEDERALLY SPONSORED RESEARCH OR DEVELOPMENT

Not applicable.

BACKGROUND OF THE DISCLOSURE

The present disclosure generally relates to a nerve coaptation apparatus and, more particularly, to a microsuture-less nerve coaptation apparatus having relatively-movable coupling members to inhibit nerve compression in the event of, for example, nerve swelling.

Microsurgery (that is, surgery aided by use of a microscope) is used in various types of medical procedures that treat relatively small bodily structures, such as coaptation of severed nerves. In this case, the procedure typically involves using a relatively small suture to connect the severed ends of the severed nerve segments. This facilitates axonal growth to fuse the nerve segments, which ideally restores some degree of nerve functionality.

Unfortunately, nerve coaptation microsutures have several limitations. For example, connecting severed nerve segments with a microsuture is a relatively long procedure that requires considerable surgical experience. Furthermore, the outcome of such procedures are typically considered poor due to relatively long recovery times (for example, up to several years) and limited nerve functionality (for example, less than 20 percent of original nerve functionality).

Nerve coaptation couplings have been proposed for use in addition to microsutures in an attempt to address the above limitations. Such couplings typically include a sleeve that houses and isolates the ends of the severed nerve segments, and pharmaceutical agents can be incorporated into the sleeve to promote axonal growth. Unfortunately, such devices inhibit nerve swelling proximate the ends of the severed nerve segments, which inwardly compresses the nerve segments and can adversely affect nerve regeneration.

Considering the above, what is needed is a nerve coaptation apparatus that addresses one or more of the shortcomings of microsutures and previous coaptation devices.

SUMMARY OF THE INVENTION

The present invention generally provides an apparatus for coaptation of first and second severed nerve segments. The apparatus includes a plurality of nerve-engaging features or "coupling members" that each connect to another coupling member to form "coupling pairs". The coupling pairs are advantageously movable relative to each other to permit nerve swelling and inhibit nerve compression.

In one aspect, the present invention provides an apparatus for coaptation of a first nerve segment separated from a second nerve segment. The apparatus includes a first coaptation member configured to extend about the first nerve segment and engage the first nerve segment. The apparatus further includes a second coaptation member configured to connect to the first coaptation member and extend about the second nerve segment. The second coaptation member includes a first coupling member and a second coupling member that are each configured to engage the second nerve segment to inhibit the second nerve segment from moving away from the first nerve segment in a longitudinal direction. The first coupling member and the second coupling member are movable relative to each other in a transverse direction substantially perpendicular to the longitudinal direction to inhibit nerve compression.

In another aspect, the present invention provides an apparatus for coaptation of a first nerve segment separated from a second nerve segment. The apparatus includes a first coaptation member configured to extend about the first nerve segment, and the first coaptation member includes a first coupling member configured to engage the first nerve segment. The apparatus further includes a second coaptation member configured to extend about the second nerve segment, and the second coaptation member includes a second coupling member configured to engage the second nerve segment. The second coupling member connects to the first coupling member to inhibit the first and second coaptation members from moving apart in a longitudinal direction and to inhibit the first and second nerve segments from moving apart in the longitudinal direction. The first coupling member and the second coupling member are movable in a transverse direction substantially perpendicular to the longitudinal direction to inhibit nerve compression.

In yet another aspect, the present invention provides an apparatus for coaptation of a first nerve segment separated from a second nerve segment. The apparatus includes a first coupling pair having a first coupling member configured to connect to the first nerve segment and a second coupling member configured to connected to the second nerve segment. The first coupling member connects to the second coupling member to engage the first nerve segment with the second nerve segment. The apparatus further includes a second coupling pair having a third coupling member configured to connect to the first nerve segment and a fourth coupling member configured to connected to the second nerve segment. The third coupling member connects to the fourth coupling member to engage the first nerve segment with the second nerve segment. The first coupling pair is movable relative to the second coupling pair to inhibit compression of the first nerve segment and the second nerve segment.

The foregoing and other objects and advantages of the invention will appear in the detailed description that follows. In the description, reference is made to the accompanying drawings that illustrate a preferred configuration of the invention.

BRIEF DESCRIPTION OF THE DRAWINGS

The present invention will hereafter be described with reference to the accompanying drawings, wherein like reference numerals denote like elements, and:

FIG. 4 is an end view of one of the coaptation members of FIG. 2;

FIG. 5 is a detail view of the area of one of the coaptation members enclosed by line 5-5 of FIG. 2;

DETAILED DESCRIPTION OF THE INVENTION

Figure 1:
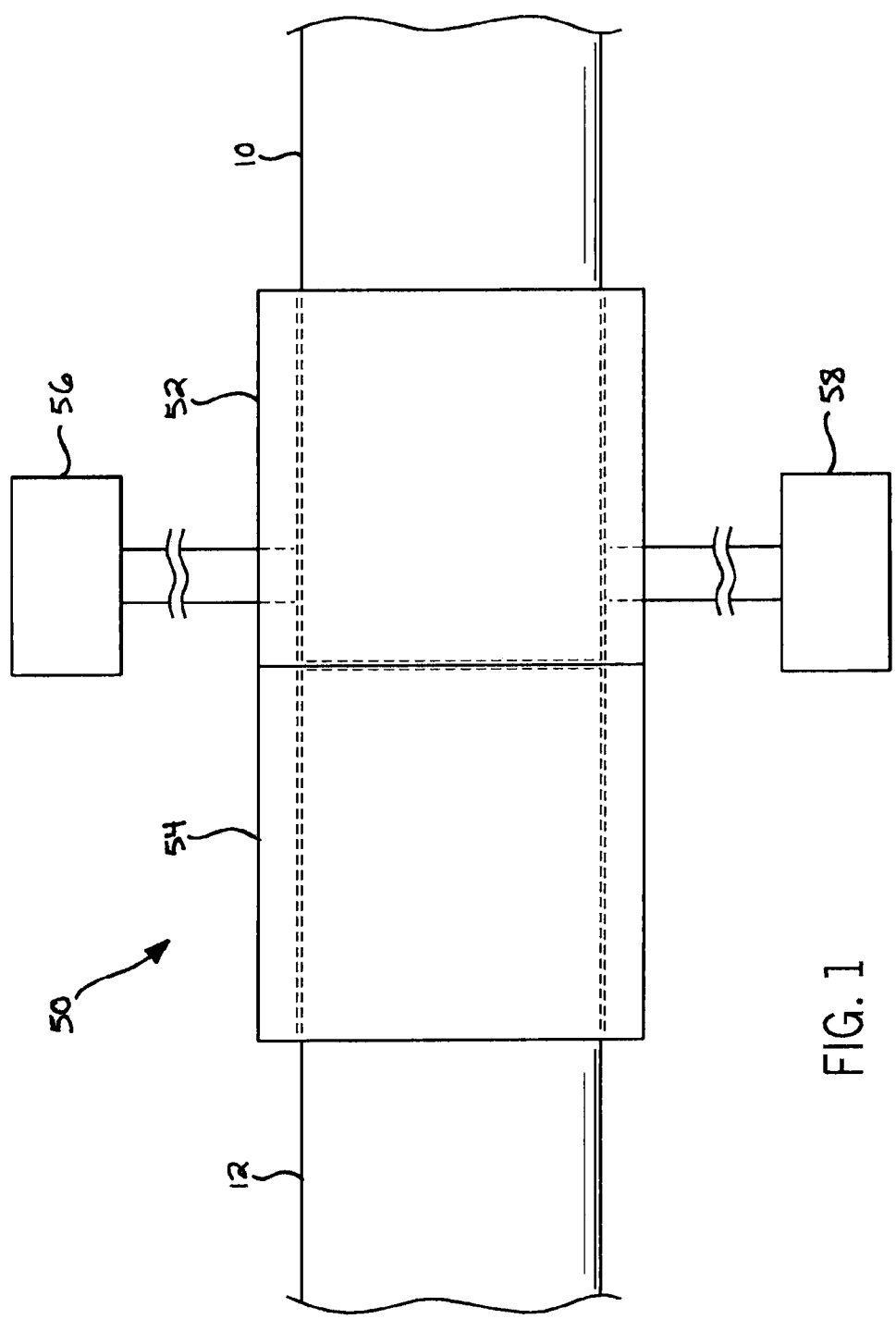
FIG. 1 is a side schematic view of a nerve coaptation apparatus according to the present invention.
Figure 2:
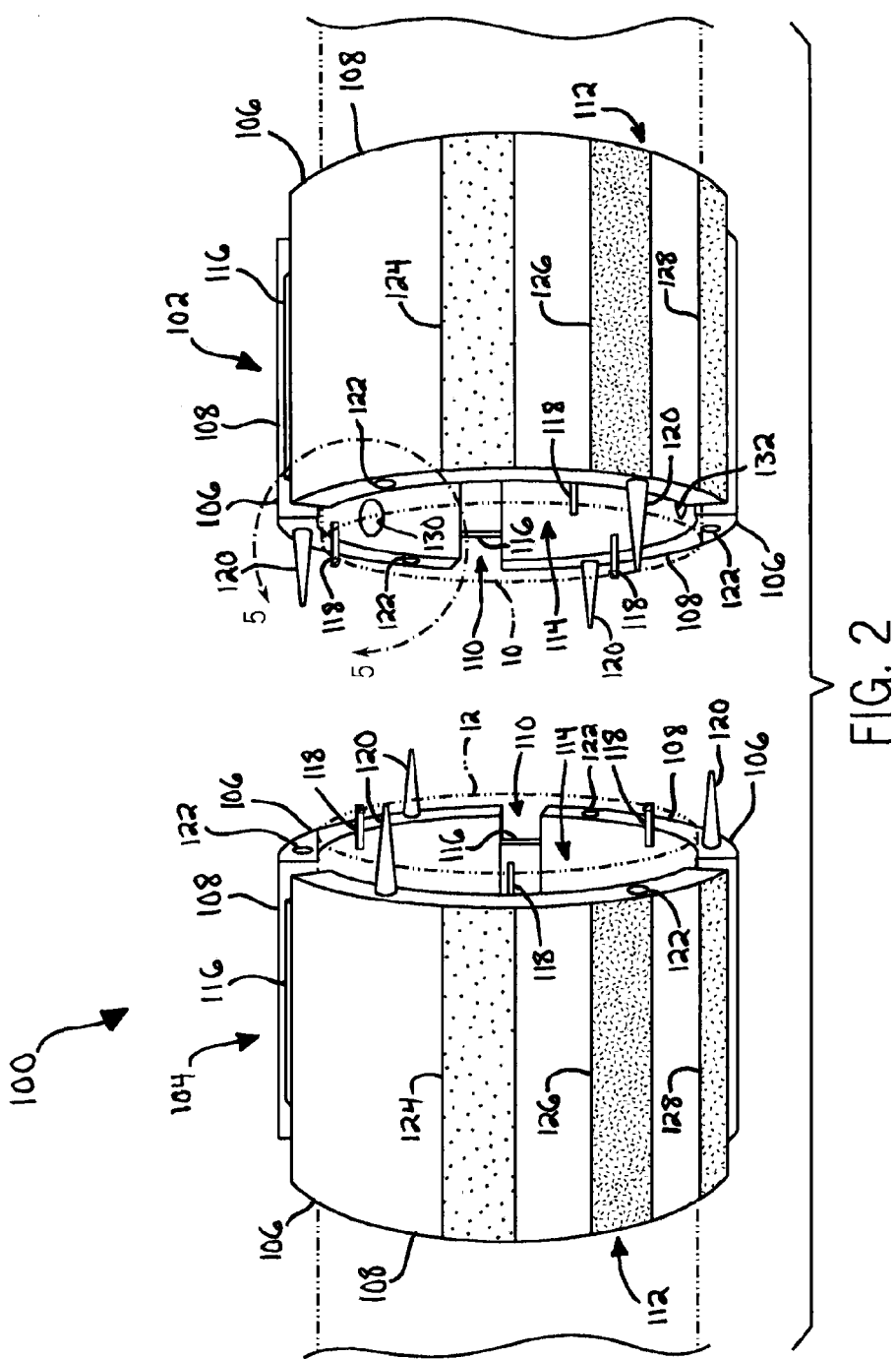
FIG. 2 is a side perspective view of a first configuration of the nerve coaptation apparatus of FIG. 1 before connecting two coaptation members.
Figure 3:
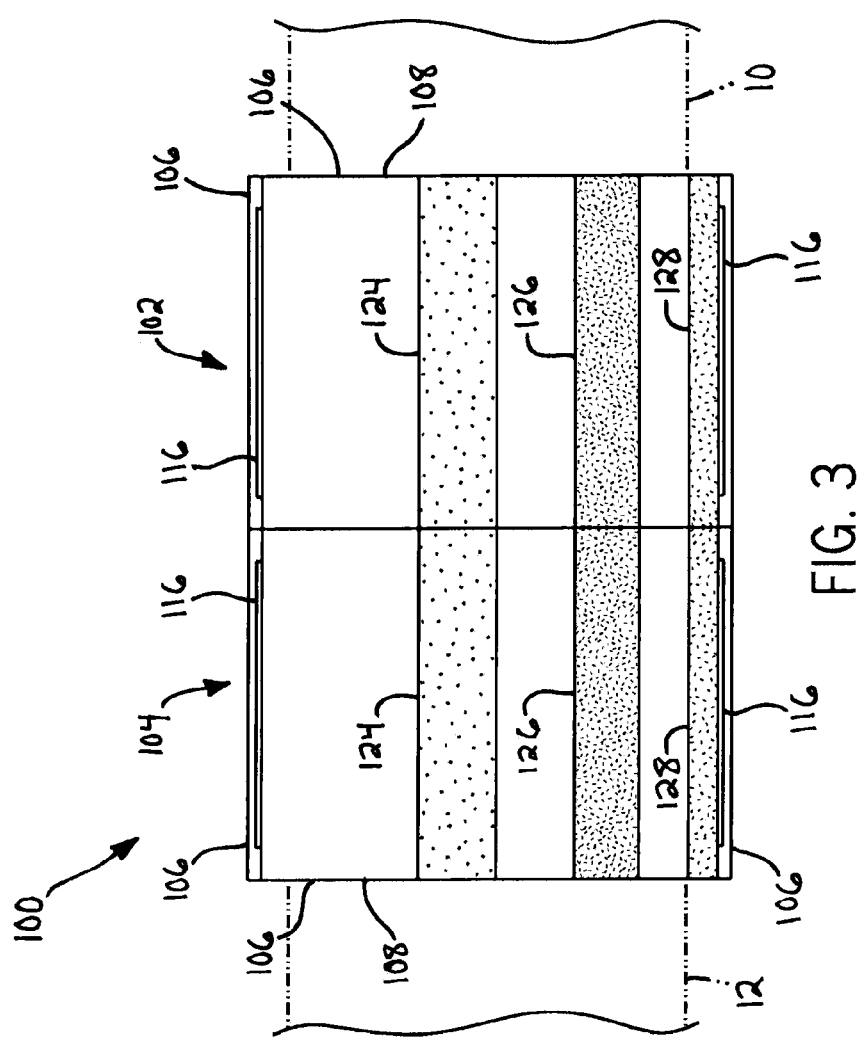
FIG. 3 is a side view of the first configuration of the nerve coaptation apparatus of FIG. 2 upon connecting the two coaptation members.
Figure 6:
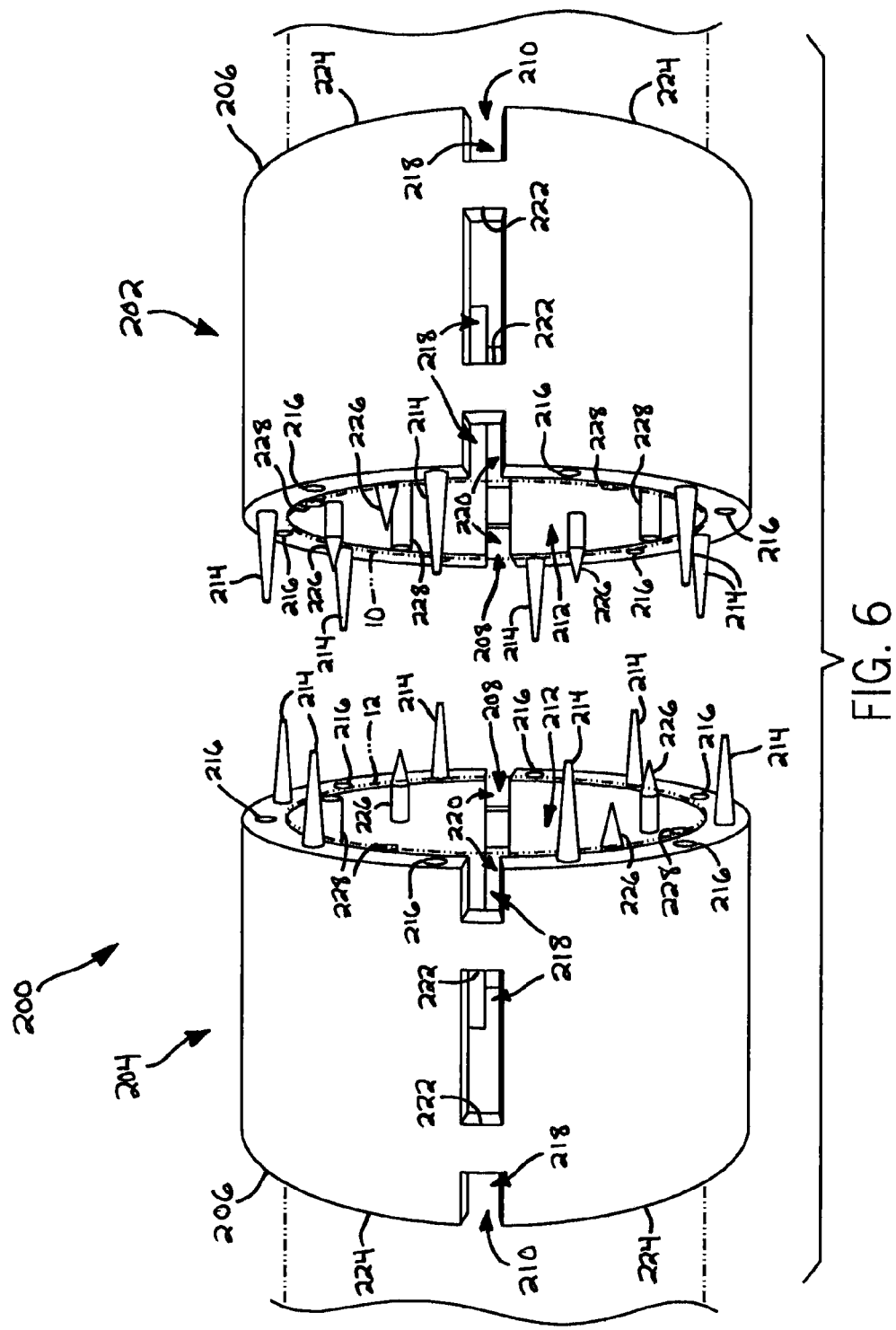
FIG. 6 is a side perspective view of a second configuration of the nerve coaptation apparatus of FIG. 1 before connecting two coaptation members.
Figure 7:
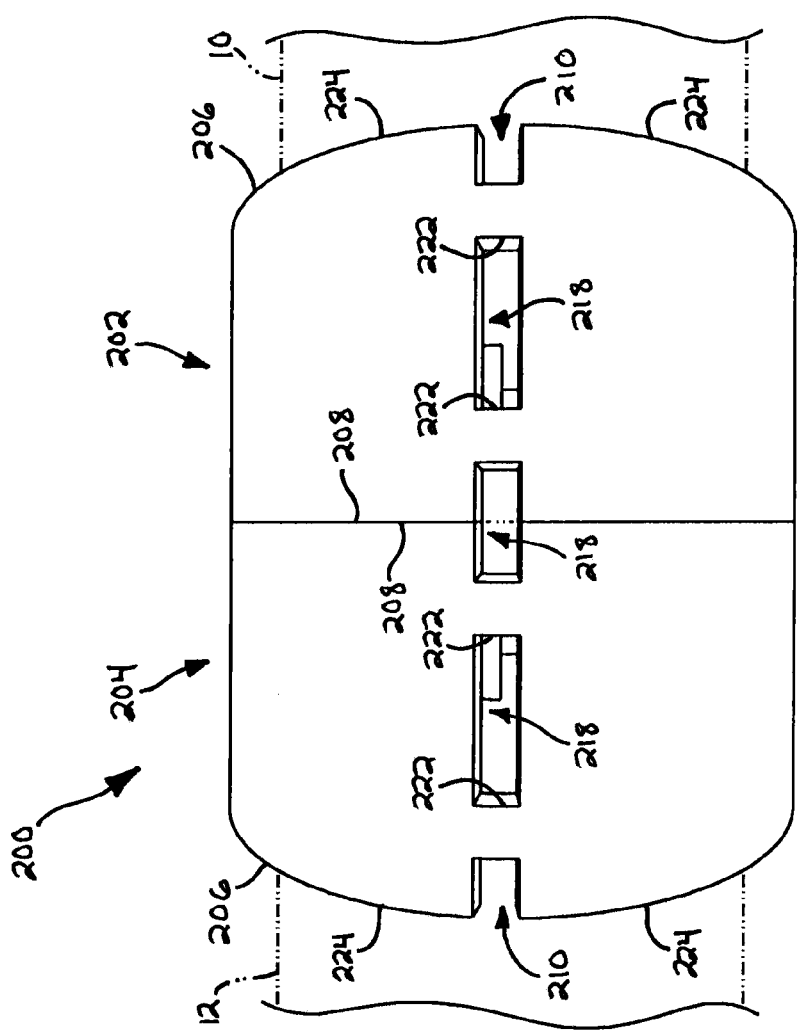
FIG. 7 is a side perspective view of the second configuration of the nerve coaptation apparatus of FIG. 6 upon connecting the two coaptation members.
Figure 8:
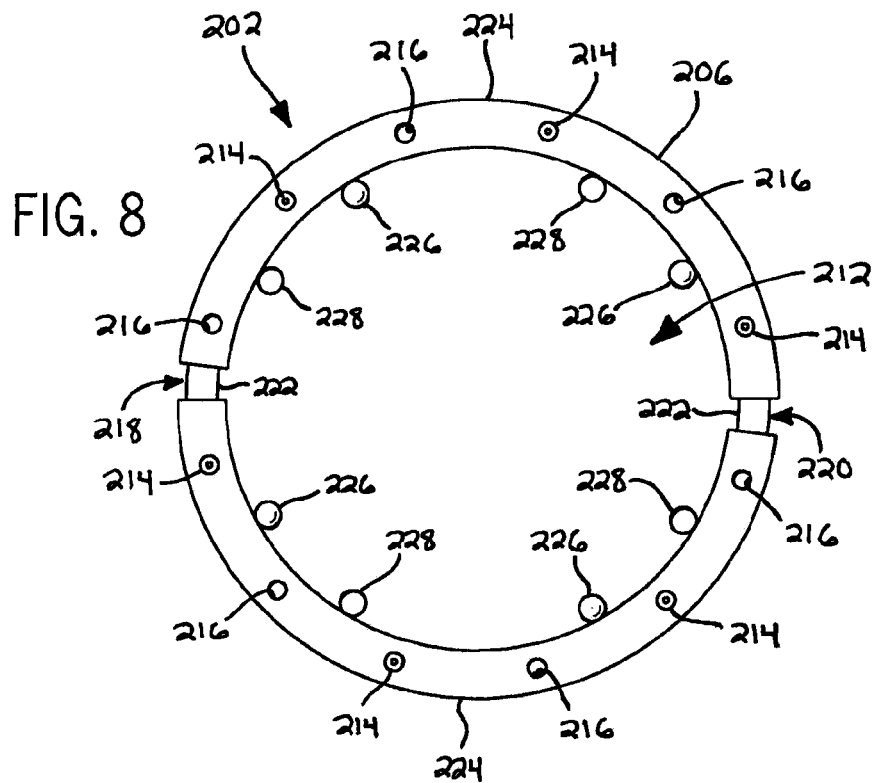
FIG. 8 is an end view of one of the coaptation members of FIG. 6.
Figure 9:
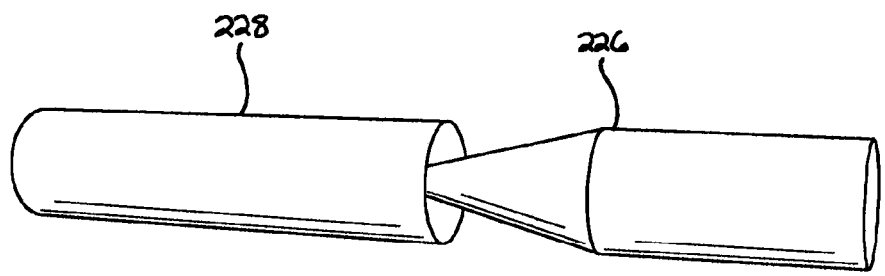
FIG. 9 is a perspective view of two coupling members of the second configuration of the nerve coaptation apparatus of FIG. 6.

Referring now to FIG. 1, the present invention provides an apparatus 50 for coaptation of first and second severed nerve segments 10, 12. Generally, the apparatus 50 includes a first coaptation member 52 that surrounds and engages the first nerve segment 10 and a second coaptation member 54 that surrounds and engages the second nerve segment 12. The first and second coaptation members 52, 54 abut each other to coapt the ends of the first and second nerve segments 10, 12. In addition, the first and second coaptation members 52, 54 include nerve-engaging features or "coupling members" that each connect to a coupling member on the opposite coaptation member 52, 54 to form "coupling pairs". The coupling pairs are advantageously movable relative to each other to permit nerve swelling and inhibit nerve compression. Various configurations of the apparatus 50 and the coupling members are described below.

The coaptation members 52, 54 also receive one or more pharmaceutical agents from an agent delivery device 56 to facilitate repair and fusion of the nerve segments 10, 12. Various pharmaceutical agents may be used, although advantageous pharmaceutical agents are described below. Regardless of the specific type used, the pharmaceutical agents are subsequently evacuated to a collection device 58.

Turning now to FIGS. 2-5, a first configuration of the nerve coaptation apparatus 100 is shown. In this configuration, the first and second coaptation members 102, 104 are generally similar, and therefore only the first coaptation member 102 is described in detail herein.

The first coaptation member 102 includes a plurality of coupling members 106, which may comprise various materials commonly associated with medical devices, such as implantable, biodegradable, and non-neurotoxic polymers and the like. Each of the coupling members 106 includes a semi-cylindrical wall 108, and together the walls 108 provide the first coaptation member 102 with a cylindrical shape for receiving the first nerve segment 10. That is, the coupling members 106 together define open ends 110, 112 through which the nerve segment 10 extends and an internal nerve passageway 114 that receives nerve segment 10. Furthermore, the coupling members 106 together define a longitudinal direction of the coaptation member 102 extending between the open ends 110, 112 and aligned with the longitudinal direction of the nerve segment 10.

To permit the coupling members 106 to move relative to each other, the first coaptation member 102 includes a plurality of expandable or flexible joints 116 connecting the sides of adjacent coupling members 106. The flexible joints 116 may comprise various materials, such as elastically deformable, implantable, biodegradable, and non-neurotoxic polymers and the like. In any case, the flexible joints 116 permit the coupling members 106 to move in a transverse direction (that is, a direction perpendicular to the longitudinal direction within five degrees) relative to one another. Such relative motion between the coupling members 106 advantageously permits nerve swelling (by up to, for example, 50 percent) and inhibits nerve compression.

The first coaptation member 102 includes several features to engage the first nerve segment 10 and the second coaptation member 104 proximate the open end 110. To connect to the nerve segment 10, each of the coupling members 106 includes a hooked epineurium pin 118. As the name implies, each epineurium pin 118 pierces the epineurium of the nerve segment 10. As such, the epineurium pins 118 inhibit the nerve segment 10 from moving longitudinally relative to the coaptation member 102. In addition, the epineurium pins 118 hold the nerve segment 10 in an appropriate position for coaptation with the second nerve segment 12 (that is, proximate the open end 110) when the coaptation members 102, 104 are connected.

To connect the first coaptation member 102 to the second coaptation member 104, each of the coupling members 106 includes two longitudinally extending connection elements 120, 122 proximate the first open end 110. Half of the connection elements are tapering posts 120 and half of the connection elements are holes 122. Each hole 122 receives one of the tapering posts 120 on the second coaptation member 104, and each tapering post 120 is received in one of the holes 122 on the second coaptation member 104. In addition, each tapering post 120 may be press-fittingly received in the corresponding hole 122 to provide a firm connection between the coaptation members 102, 104. Such a connection may inhibit the coaptation members 102, 104 from moving apart in the longitudinal direction once connected.

One or more of the coupling members 106 also include features to ensure proper angular alignment of the nerve segments 10, 12 (that is, proper alignment of individual axons and the like). Specifically, on each of the coaptation members 102, 104, one of the coupling members 106 includes a plurality of strips 124, 126, and 128 of different colors. When connecting the nerve segments 10, 12 to the coaptation members 102, 104, respectively, common features of the nerve segments 10, 12 (for example, fascicle patterns or the like) may be aligned with a specific strip 124, 126, or 128. Then, when connecting the coaptation members 102, 104 to each other, matching color strips 124, 126, and 128 on the coaptation members 102, 104 are aligned to ensure that the features of the nerve segments 10, 12 are aligned. Furthermore, the coupling members 106 could be translucent or transparent to permit the nerve segments 10, 12 to be viewed therethrough.

During deployment, the coaptation members 102, 104 may be moved towards each other and joined using a linear or hinged coupling applicator, such as those used for vascular anastomoses. Other deployment devices may alternatively be used.

After deployment, one or more pharmaceutical agents may be delivered from the agent delivery device, through an inlet passageway 130 defined by one of the coupling members 106, and into the nerve passageways 114 to facilitate repair and fusion of the nerve segments 10, 12. After a specified amount of time, the pharmaceutical agents are evacuated through an outlet passageway 132 defined by one of the coupling members 106 and into the collection device.

The first configuration of the nerve coaptation apparatus 100 may be modified in other manners that are not explicitly described above. For example, the coupling members 106 may include more or less than two connection elements 120, 122 and one epineurium pin 118 (for example, each coaptation member 102 and 104 may include twelve connection elements 120, 122 and six epineurium pins 118). As another example, the inlet passageway 130 and outlet passageway 132 may be omitted, and gaps defined by the flexible joints 116 and the sides of adjacent coupling members 106 may serve as inlet and outlet passageways.

Turning now to FIGS. 6-9, a second configuration of the nerve coaptation apparatus 200 is shown. In this configuration, the apparatus 200 includes a first coaptation member and a second coaptation member 202, 204 that are generally similar. As such, only the first coaptation member 202 is described in detail herein. In general, the first coaptation member 202 permits nerve swelling and inhibits compression by deploying a plurality of relatively movable coupling members. This aspect is described in further detail below.

The first coaptation member 202 may comprise various materials commonly associated with medical devices, such as non-neurotoxic polymers and the like. The first coaptation member 202 includes a wall 206 that defines a cylindrical shape for receiving the first nerve segment 10. That is, the wall 206 defines open ends 208, 210 through which the nerve segment 10 extends and an internal nerve passageway 212 that receives nerve segment 10. Furthermore, the coaptation member 202 defines a longitudinal direction extending between the open ends 208, 210 and aligned with the longitudinal direction of the nerve segment 10.

The first coaptation member 202 also supports connection elements 214, 216, such as those described above, to connect to the second coaptation member 204. That is, the coaptation member 202 includes a plurality of longitudinally extending connection elements 214, 216 proximate the first open end 208. Half of the connection elements are tapering posts 214 and half of the connection elements are holes 216. Each hole 216 receives one of the tapering posts 214 on the second coaptation member 204, and each tapering post 214 is received in one of the holes 216 on the second coaptation member 204. In addition, each tapering post 214 may be press-fittingly received in the corresponding hole 216 to provide a firm connection between the coaptation members 202, 204. Such a connection may inhibit the coaptation members 202, 204 from moving apart in the longitudinal direction once connected.

The first coaptation member 202 also includes inlet and outlet passageways 218, 220 to receive and evacuate one or more pharmaceutical agents, respectively. In this configuration, the inlet and outlet passageways 218, 220 are defined adjacent to bridges 222 that connect opposite semi-cylindrical halves 224 of the coaptation member 202.

As described briefly above, the first coaptation member 202 releasably supports a plurality of coupling members 226, 228 on the inner surface of the wall 206. The coupling members 226, 228 engage and hold the first nerve segment 10 in contact with the second nerve segment 12. As such, the coupling members 226, 228 may comprise various materials commonly associated with medical devices, such as implantable, biodegradable, and non-neurotoxic polymers and the like.

To engage and hold the first nerve segment 10 in contact with the second nerve segment 12, half of the coupling members 226 have tapering shapes and act as epineurium pins that pierce the epineurium of the nerve segment 10. In addition, these coupling members 226 are fixedly received by a corresponding pin-receiving coupling member 228 of the second coaptation member 204. Similarly, each pin-receiving coupling member 228 of the first coaptation member 202 fixedly receives one of the epineurium pin coupling members 226 of the second coaptation member 204.

After receiving the nerve segments 10, 12, connecting to each other, and delivering and evacuating the pharmaceutical agents, the coaptation members 202, 204 detach from the coupling members 226, 228, for example, by breaking the bridges 222 and an adhesive connection between the coaptation members 202, 204 and the coupling members 226, 228. The coupling members 226, 228 remain connected to each other and the nerve segments 10, 12. As such, the coupling members 226, 228 inhibit the nerve segments 10, 12 from moving apart in the longitudinal direction. However, each pair of coupling members 226, 228 is movable in the transverse direction relative to the other pairs. The coupling members 226, 228 thereby permit nerve swelling and inhibit compression.

Figure 10:
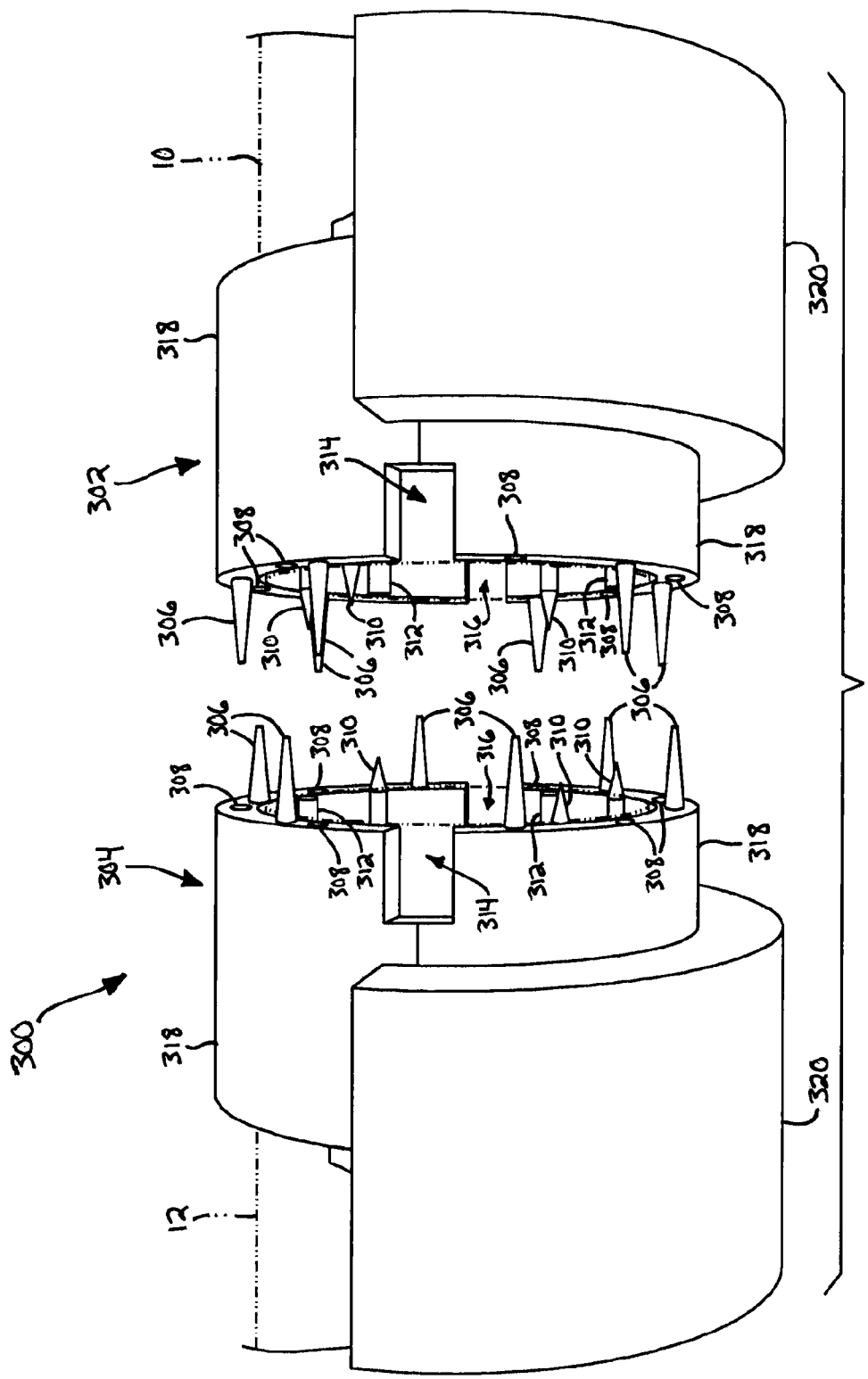
FIG. 10 is a side perspective view of a third configuration of the nerve coaptation apparatus of FIG. 1 before connecting two coaptation members.
Figure 11:
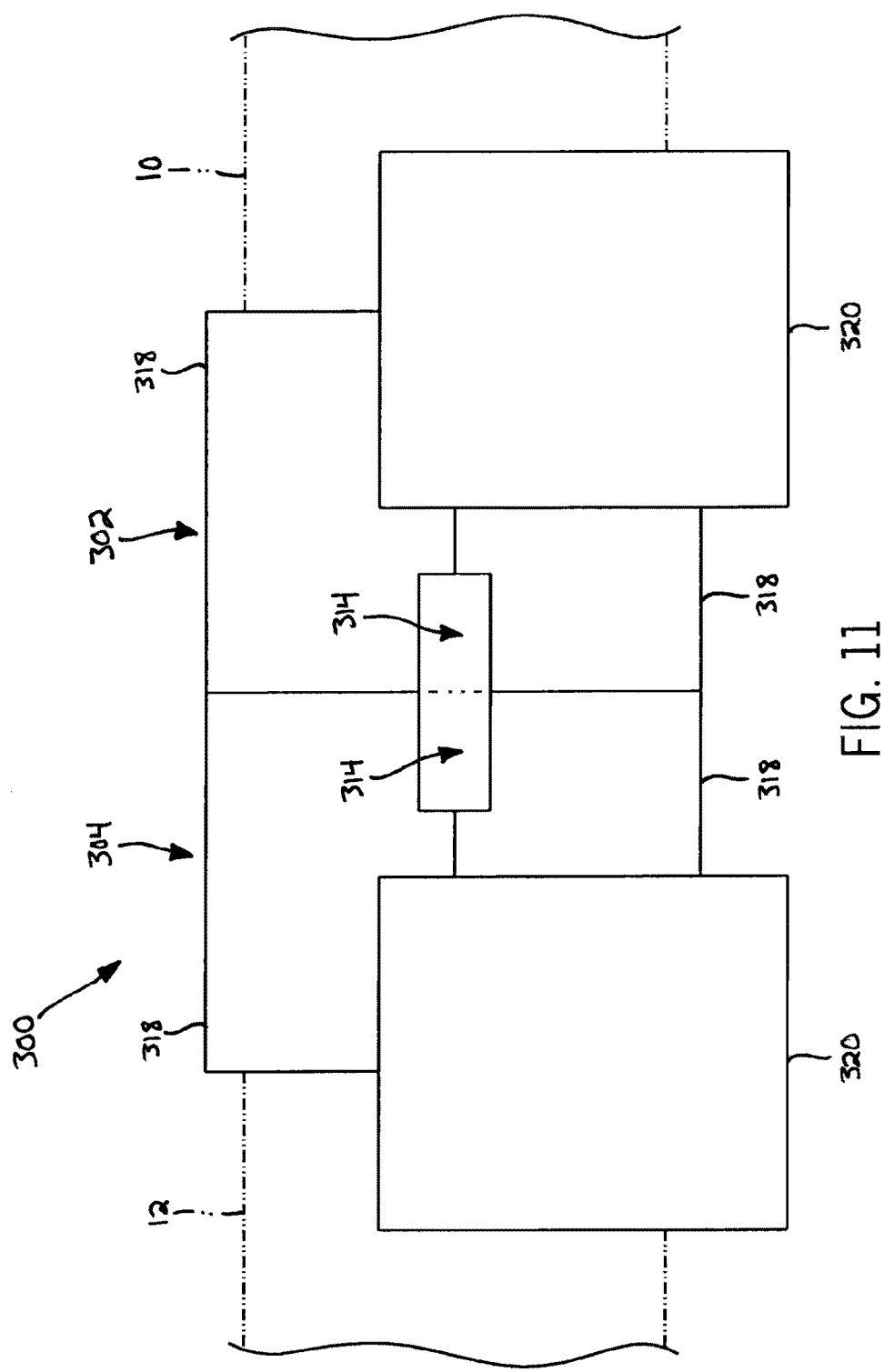
FIG. 11 is a side perspective view of the third configuration of the nerve coaptation apparatus of FIG. 10 upon connecting the two coaptation members.
Figure 12:
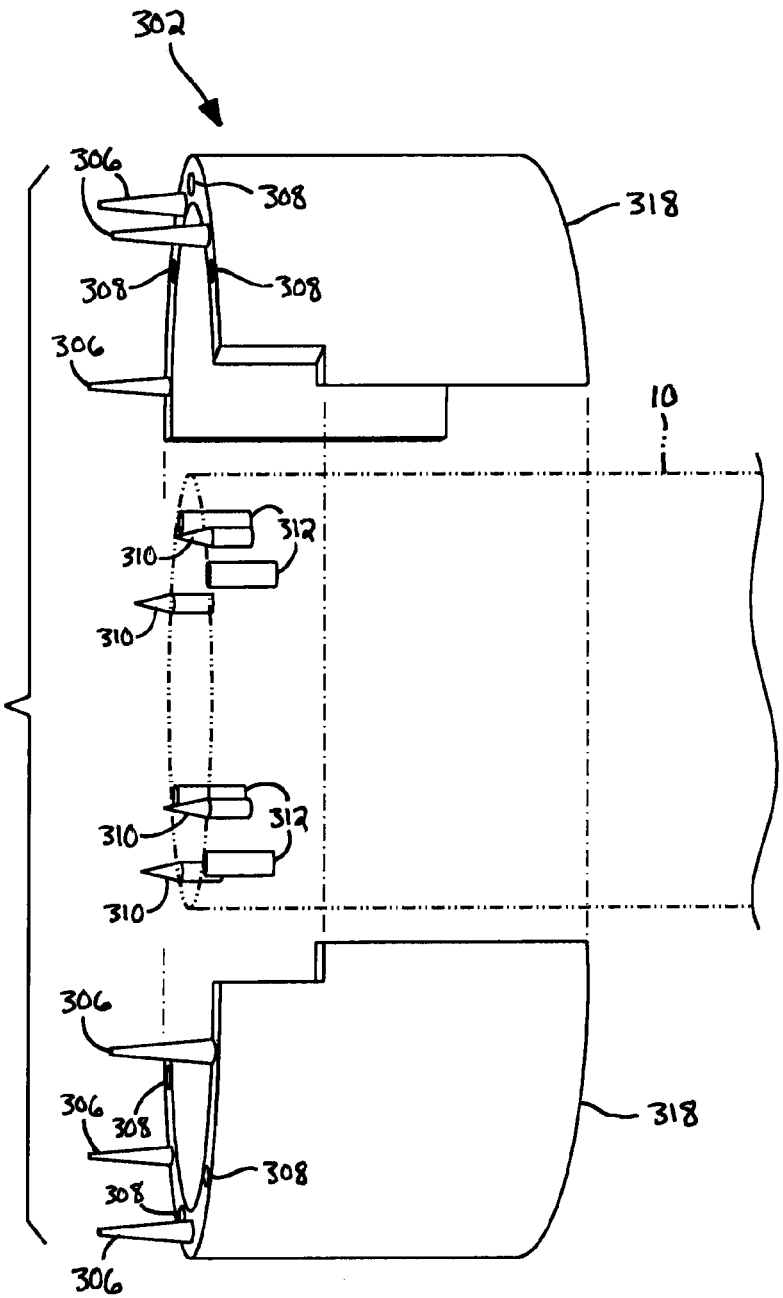
FIG. 12 is a side perspective view of separation of two halves of one of the coaptation members of FIG. 10.

Turning now to FIGS. 10-12, a third configuration of the nerve coaptation apparatus 300 is shown. The third configuration of the apparatus 300 shares many features with the second configuration of the nerve coaptation apparatus 200. For example, the coaptation members 302, 304 may comprise various materials commonly associated with medical devices, such as non-neurotoxic polymers and the like. Furthermore, each coaptation member 302, 304 includes a plurality of connection elements 306, 308 like those described above and a plurality of detachably supported and nerve-engaging coupling members 310, 312 like those described above. Each coaptation member 302, 304 also includes inlet and outlet passageways 314, 316 to receive and evacuate one or more pharmaceutical agents, respectively.

In contrast to the second configuration, each coaptation member 302, 304 includes two separate semi-cylindrical halves 318 that are initially held in abutment by a semi-cylindrical deployment element 320. As such, after connecting the nerve segments 10, 12 to the coupling members 310, 312 and connecting the coaptation members 302, 304 to each other, the deployment elements 320 are detached from the coaptation members 302, 304 by, for example, moving the deployment elements 320 apart in the longitudinal direction. Thereafter, and as shown in FIG. 12, the coaptation member halves 318 are separated from each other, the coupling members 310, 312, and the nerve segments 10, 12 by moving apart in the transverse direction.

For each of the above configurations, the coaptation members may provide a range of sizes appropriate for use with digital nerve repair (about 1 mm in diameter) up to brachial root repair (about 1 cm in diameter).

Figure 13:
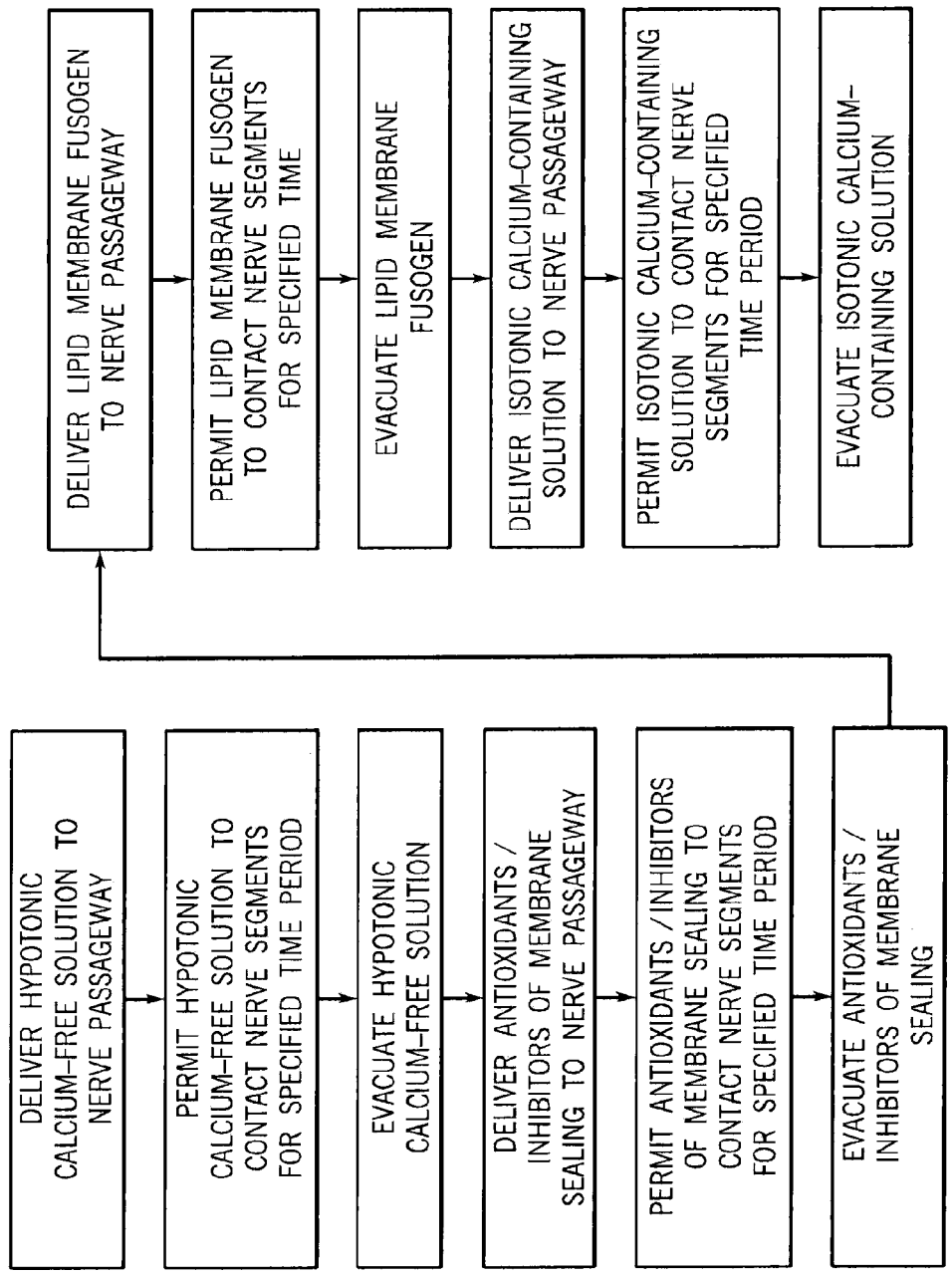
FIG. 13 is a flow chart setting forth steps of a pharmaceutical agent delivery sequence conducted by the apparatus of FIG. 1.
Figure 14B:
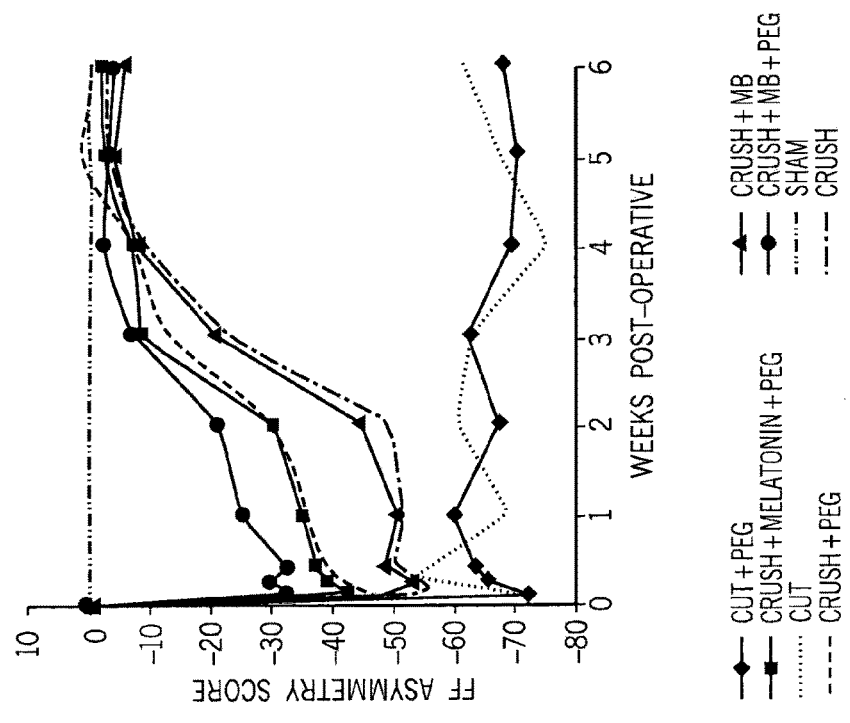
FIG. 14B is a plot of foot fault asymmetry scores versus post-operative time for various types of nerve injuries and pharmaceutical agent sequences.
Figure 14A:
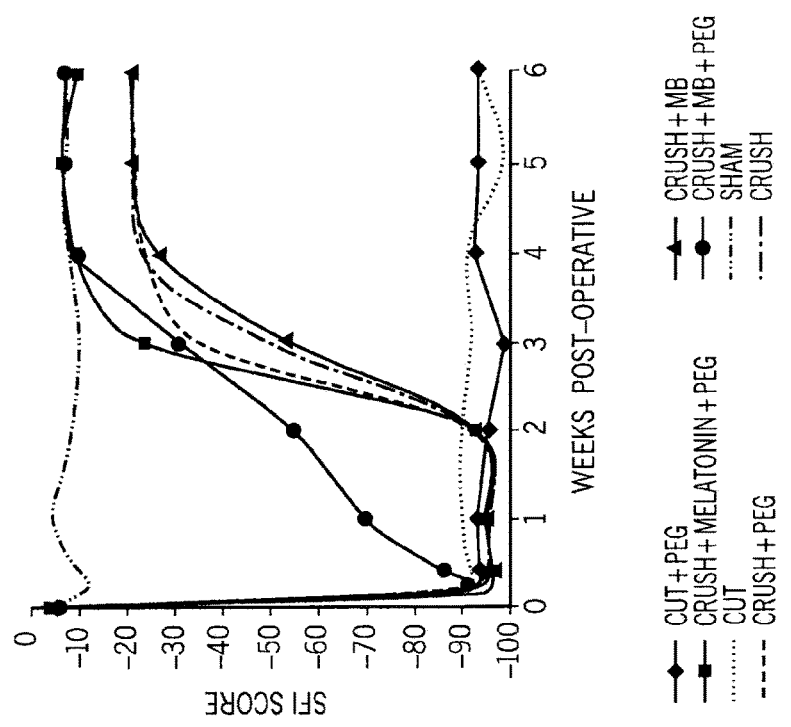
FIG. 14A is a plot of sciatic function index scores versus post-operative time for various types of nerve injuries and pharmaceutical agent sequences.

Turning now to FIGS. 13, 14A, and 14B and as briefly described above, the coaptation members may receive one or more pharmaceutical agents from the agent delivery device to facilitate repair and fusion of the nerve segments. The agent delivery device may be one or more syringes (in the case of a single syringe, multiple agents may be separately compartmentalized), a manifold that automatically delivers pharmaceutical agents, or the like.

Regardless of the specific type of agent delivery device, the pharmaceutical agents preferably and advantageously include a sequence of: 1) a hypotonic calcium-free solution (for example, a solution as shown below in Tables 1 and 2 applied for a period of about 60 seconds before evacuation); 2) antioxidants/inhibitors of membrane sealing (for example, 2 mM melatonin or 100 μM USP methylene blue applied for a period of about 90 seconds before evacuation); 3) a lipid membrane fusogen (for example, 5 g polyethylene glycol 2000 (PEG) dissolved in 5 mL distilled water applied for about 90 seconds before evacuation); and; 4) isotonic calcium-containing solution (for example, a solution as shown below in Tables 3-5 applied for a period of about 120-180 seconds before evacuation).

TABLE 1

Hypotonic calcium-free solution. Chemicals dissolved in 1000 mL distilled water, buffering pH with HCl or NaOH, respectively, added drop-wise.

| Symbol | Chemical | Amount | MW | Factor | mM/L | species | mOsm/L |
|---|---|---|---|---|---|---|---|
| NaCl | Sodium Chloride | 5.7856 g | 58.44 | 1 | 99 | 2 | 198 |
| KCl | Potassium Chloride | 0.3728 g | 74.56 | 1 | 5 | 2 | 10.0 |
| $KH_2PO_4$ | Potassium Phosphate | 0.1634 g | 136.09 | 1 | 1.2 | 2 | 2.4 |
| $MgSO_4$ | Magnesium Sulfate | 0.1566 g | 120.39 | 1 | 1.3 | 2 | 2.6 |
| $NaHCO_3$ | Sodium Bicarbonate | 2.1842 g | 84.01 | 1 | 25 | 2 | 50.0 |
| $NaC_6H_7O_6$ | Sodium Ascorbate | 1.981 g | 198.1 | 1 | 10 | 2 | 20.0 |
| $C_6H_{12}O_6$ | Dextrose | 1.8 g | 180.16 | 1 | 9.9 | 1 | 10.0 |
| — | Solution A (see Table 2) | 50 mL | 95.21 | 85.49/10 | 8.55 | 3 | 25.7 |
| | | | | | | | 273.7 |
| | | | | | | | 318.7 |

TABLE 2

Solution A. Dissolved in 500 mL distilled water.

| Symbol | Chemical | Amount (g) | MW | Multiplicand | mM/L | Species | mOsm/L |
|---|---|---|---|---|---|---|---|
| $MgCl_2$ | Magnesium Chloride | 4.07 | 95.21 | 2 | 85.49 | 3 | 256.47 |

TABLE 3

Isotonic calcium-containing solution. Buffer pH with HCl or NaOH, respectively, added drop-wise. Mix cold.

| Symbol | Chemical | Amount | MW | mM/L | Species | mOsm/L |
|---|---|---|---|---|---|---|
| — | Solution B (see Table 4) | 475 mL | 473.49 | 331.55 | 1 | 314.97 |
| $H_2O$ | Distilled Water | 475 mL | 18 | — | — | |
| — | Solution C (see Table 5) | 50 mL | 111.0 | 2 | 3 | 6.0 |
| $NaC_6H_7O_6$ | Sodium Ascorbate | 1.981 g | 198.1 | 10 | 2 | 20 |
| $C_6H_{12}O_6$ | Dextrose | 1.8 g | 180.16 | 9.9 | 1 | 9.9 |
| | | | | | | 350.87 |

TABLE 4

Solution B. Chemicals dissolved in 4000 mL distilled water.

| Symbol | Chemical | Amount (g) | MW | Divisor | mM/L | Species | mOsm/L |
|---|---|---|---|---|---|---|---|
| NaCl | Sodium Chloride | 61.024 | 58.44 | 4 | 261.05 | 2 | 522.1 |
| KCl | Potassium Chloride | 3.139 | 74.56 | 4 | 10.5 | 2 | 21 |

TABLE 4-continued

Solution B. Chemicals dissolved in 4000 mL distilled water.

| Symbol | Chemical | Amount (g) | MW | Divisor | mM/L | Species | mOsm/L |
|---|---|---|---|---|---|---|---|
| $KH_2PO_4$ | Potassium Phosphate | 1.374 | 136.09 | 4 | 2.52 | 2 | 5.04 |
| $MgSO_4$ | Magnesium Sulfate | 1.318 | 120.39 | 4 | 2.74 | 2 | 5.48 |
| $NaHCO_3$ | Sodium Bicarbonate | 18.394 | 84.01 | 4 | 54.74 | 2 | 109.48 |
|  |  |  | 473.49 |  | 331.55 |  | 663.1 |

TABLE 5

Solution C. Dissolved in 1000 mL distilled water.

| Symbol | Chemical | Amount (g) | MW | mM/L | Species | mOsm/L |
|---|---|---|---|---|---|---|
| $CaCl_2$ | Calcium Chloride | 4.44 | 111.0 | 40 | 3 | 120 |

Alternatively, the hypotonic calcium-free solution may be additionally applied to the nerve after the antioxidants/inhibitors of membrane sealing and before the lipid membrane fusogen to wash away USP methylene blue stains on the nerve segments.

Data collected by the present inventors and partially illustrated in FIGS. 14A and 14B indicates that antioxidants/inhibitors of membrane sealing, such as USP methylene blue and melatonin, maintain the axonal ends of severed nerve segments in an open and vesicle-free state appropriate for repair by a lipid membrane fusogen, such as PEG. Furthermore, these data also indicate that the above sequence advantageously improves recovery time and nerve function compared to microsutures, specifically by a factor of up to two and 40 percent in four months, respectively.

After the specified contact period with the nerve segments, each pharmaceutical agent may be evacuated by applying vacuum pressure, permitting free drainage, capillary action (for example, by connecting the outlet passageway to an absorbent surgical material), or the like. Furthermore, the actions of the delivery device and the collection device can be coordinated, for example, via an electronic controller (not shown) and a plurality of valves (not shown), such that each pharmaceutical agent contacts the nerve segments for the specified contact period. Such a controller may also control the delivery pressure of the pharmaceutical agents. That is, the controller may provide the agents at a pressure sufficiently low to maintain contact of the ends of the nerve segments, and sufficiently high to ensure adequate distribution of the chemicals over the nerve segments.

The pharmaceutical agent delivery sequence may be summarized as follows.

A method for treatment of a nerve, comprising the steps of:
 delivering at least one of an antioxidant and an inhibitor of membrane sealing to the nerve;
 evacuating the at least one of the antioxidant and the inhibitor of membrane sealing away from the nerve;
 delivering at least one lipid membrane fusogen to the nerve after evacuating the at least one of the antioxidant and the inhibitor of membrane sealing; and
 evacuating the at least one lipid membrane fusogen away from the nerve.

In some configurations, the at least one of the antioxidant and the inhibitor of membrane sealing includes one of USP methylene blue and melatonin.

In some configurations, the at least one lipid membrane fusogen includes polyethylene glycol.

In some configurations, the method further comprises the steps of:
 delivering at least one hypotonic calcium-free solution to the nerve; and
 evacuating the at least one hypotonic calcium-free solution away from the nerve before delivering the at least one of the antioxidant and the inhibitor of membrane sealing.

In some configurations, the method further comprises the steps of:
 delivering at least one isotonic calcium-containing solution to the nerve after evacuating the at least one lipid membrane fusogen; and
 evacuating the at least one isotonic calcium-containing solution away from the nerve.

In some configurations, the nerve includes a first segment severed from and abutting a second segment, and each of the at least one of the antioxidant and the inhibitor of membrane sealing and the at least one lipid membrane fusogen are delivered to and evacuated away from the first segment and the second segment.

The pharmaceutical agents may be provided in a kit. Such a kit may be summarized as follows.

A kit for use in a pharmaceutical agent delivery sequence, comprising:
 at least one of an antioxidant and an inhibitor of membrane sealing;
 at least one lipid membrane fusogen; and
 instructions indicating that the pharmaceutical agent delivery sequence includes at least one of the antioxidant and the inhibitor of membrane sealing followed by the at least one lipid membrane fusogen.

From the above description, it should be apparent that the present invention provides a nerve coaptation apparatus that includes a plurality of nerve-engaging coupling pairs. The coupling pairs are advantageously movable relative to each other to permit nerve swelling and inhibit nerve compression.

The various configurations presented above are merely examples and are in no way meant to limit the scope of this disclosure. Variations of the configurations described herein will be apparent to persons of ordinary skill in the art, such variations being within the intended scope of the present application. In particular, features from one or more of the above-described configurations may be selected to create alternative configurations comprised of a sub-combination of features that may not be explicitly described above. In addition, features from one or more of the above-described configurations may be selected and combined to create alternative configurations comprised of a combination of features which may not be explicitly described above. Features suitable for such combinations and sub-combinations would be readily apparent to persons skilled in the art upon review of the present application as a whole. The subject matter described herein and in the recited claims intends to cover and embrace all suitable changes in technology.

What is claimed is:

1. A method of coaptation of a first and second nerve segments having cut but not crushed ends, said segments being segments of a nerve that has been cut but not crushed comprising the steps of:
   a) applying a hypotonic, calcium-free saline solution to said first and second cut but not crushed nerve segments of a nerve that has been cut but not crushed, for a first period of time;
   b) concurrent with or after step a), applying to said nerve segments a solution containing an antioxidant inhibitor of membrane sealing for a second period of time;
   c) bringing into contact a cut end of the first nerve segment with a cut end of the second nerve segments;
   d) then applying a lipid membrane fusogen solution to said contacted first and second nerve segments for a third period of time; and
   (e) applying to the contacted nerve segments an isotonic, calcium-containing solution for a fourth period of time, to thereby coapt said contacted nerve first and second nerve segments.

2. The method of claim 1, wherein said first and second nerve segments having cut but not crushed ends are in a human patient.

3. The method of claim 1, wherein the hypotonic, calcium-free solution comprises sodium chloride, potassium chloride, potassium phosphate, magnesium sulfate, sodium bicarbonate, sodium ascorbate, and/or dextrose.

4. The method of claim 1, wherein said lipid membrane fusogen comprises polyethylene glycol (PEG).

5. The method of claim 4, wherein the PEG is present at a concentration of from 100 to 500 mM.

6. The method of claim 1, wherein following the first, second, third and fourth periods of time, the respective solution is evacuated.

7. The method of claim 1, wherein the first period of time is about 60 seconds, the second period of time is about 90 seconds, the third period of time is about 90 seconds and the fourth period of time is about 120 to 180 seconds.

8. The method of claim 1, wherein the lipid membrane fusogen is applied for about 90 seconds before evacuation.

9. The method of claim 1, wherein the isotonic, calcium-containing solution is applied for about 120-180 seconds before evacuation.

10. The method of claim 1, further comprising a further application of a hypotonic calcium-free solution to the nerve after step b) and/or after step c).

11. The method of claim 1, wherein the solutions are contained within syringes.

12. The method of claim 1, wherein the hypotonic, calcium-free saline and the solution containing an antioxidant are comprised in separate barrels of a double-barreled syringe.

13. The method of claim 1, wherein the antioxidant is methylene blue.

14. The method of claim 1, wherein the antioxidant is melatonin.

15. A method of coaptation of a first and second nerve segments having cut but not crushed ends, said segments being segments of a nerve that has been cut but not crushed comprising the steps of:
   a) applying a hypotonic, calcium-free saline solution to said first and second cut nerve segments of a nerve that has been cut but not crushed, for a first period of time;
   b) bringing into contact the cut end of the first nerve segment with the cut end of the second nerve segments;
   c) after step a), applying to said nerve segments a solution containing an antioxidant inhibitor of membrane sealing and a lipid membrane fusogen for a second period of time;
   d) applying to the contacted nerve segments an isotonic, calcium-containing solution for a fourth period of time, to thereby coapt said contacted nerve first and second nerve segments.

16. A method of coaptation of a first and second nerve segments, said segments being segments of a nerve, the method comprising the steps of:
   a) applying a hypotonic, calcium-free saline solution to said first and second nerve segments for a first period of time;
   b) concurrent with or after step a), applying to said nerve segments a solution containing an antioxidant inhibitor of membrane sealing for a second period of time;
   c) bringing into contact ends of the first and second nerve segments;
   d) then applying a lipid membrane fusogen solution to said contacted first and second nerve segments for a third period of time; and
   (e) applying to the contacted nerve segments an isotonic, calcium-containing solution for a fourth period of time, to thereby coapt said contacted first and second nerve segments.

17. The method of claim 16, wherein the antioxidant is methylene blue.

18. The method of claim 16, wherein the antioxidant is melatonin.

19. The method of claim 16, wherein the hypotonic, calcium-free solution comprises sodium chloride, potassium chloride, potassium phosphate, magnesium sulfate, sodium bicarbonate, sodium ascorbate, and/or dextrose.

20. The method of claim 19, further comprising a further application of a hypotonic calcium-free solution to the nerve after step b) and/or after step c).

21. The method of claim 16, wherein said lipid membrane fusogen comprises polyethylene glycol (PEG).

22. The method of claim 21, wherein the PEG is present at a concentration of from 100 to 500 mM.

23. The method of claim 16, wherein following the first, second, third and fourth periods of time, the respective solution is evacuated.

24. The method of claim 23, wherein the first period of time is about 60 seconds, the second period of time is about 90 seconds, the third period of time is about 90 seconds and the fourth period of time is about 120 to 180 seconds.

25. The method of claim 16, wherein said first and second nerve segments are in a human patient.

* * * * *